United States Patent
Ostiguy, Jr. et al.

[11] Patent Number: 6,152,961
[45] Date of Patent: Nov. 28, 2000

[54] ACETABULAR PROSTHESIS ASSEMBLY

[75] Inventors: Pierre S. Ostiguy, Jr., Rochester; Robert E. Sommerich, Norton, both of Mass.

[73] Assignee: Depuy Orthopaedics, Inc., Warsaw, Ind.

[21] Appl. No.: 08/998,881

[22] Filed: Dec. 29, 1997

[51] Int. Cl.⁷ .................................................. A61F 2/34
[52] U.S. Cl. ................................ 623/22.28; 623/22.21; 623/22.17; 623/22.19
[58] Field of Search ................................ 623/16, 18, 19, 623/22

[56] References Cited

U.S. PATENT DOCUMENTS

| | | | |
|---|---|---|---|
| 3,903,549 | 9/1975 | Deyerle | 623/22 |
| 4,172,296 | 10/1979 | D'Errico | 3/1.912 |
| 4,619,658 | 10/1986 | Pappas et al. | 623/22 |
| 4,650,491 | 3/1987 | Parchinski | 623/22 |
| 4,678,472 | 7/1987 | Noiles | 623/18 |
| 4,704,127 | 11/1987 | Averill et al. | 623/22 |
| 4,770,658 | 9/1988 | Geremakis | 623/22 |
| 4,784,663 | 11/1988 | Kenna | 623/22 |
| 4,795,469 | 1/1989 | Oh | 623/22 |
| 4,878,916 | 11/1989 | Rhenter et al. | 623/18 |
| 4,936,861 | 6/1990 | Muller et al. | 623/22 |
| 4,969,910 | 11/1990 | Frey et al. | 623/22 |
| 5,021,062 | 6/1991 | Adrey et al. | 623/22 |
| 5,049,158 | 9/1991 | Engelhardt et al. | 623/22 |
| 5,171,285 | 12/1992 | Broderick | 623/22 |
| 5,217,499 | 6/1993 | Shelley | 623/22 |
| 5,226,917 | 7/1993 | Schryver | 623/22 |
| 5,263,988 | 11/1993 | Huebner | 623/22 |
| 5,314,487 | 5/1994 | Schryver et al. | 623/22 |
| 5,360,451 | 11/1994 | Keller | 623/22 |
| 5,376,122 | 12/1994 | Pappas et al. | 623/22 |
| 5,425,779 | 6/1995 | Schlosser et al. | 623/23 |
| 5,443,519 | 8/1995 | Averill et al. | 623/22 |
| 5,480,448 | 1/1996 | Mikhail | 623/22 |
| 5,507,826 | 4/1996 | Besselink et al. | 623/22 |
| 5,549,691 | 8/1996 | Harwin | 623/22 |
| 5,549,698 | 8/1996 | Averill et al. | 623/22 |
| 5,658,348 | 8/1997 | Rohr, Jr. | 623/22 |
| 5,879,405 | 3/1999 | Ries et al. | 623/22 |
| 5,935,175 | 8/1999 | Ostiguy, Jr. et al. | 623/22 |
| 5,938,702 | 8/1999 | Lopez et al. | 623/22 |

FOREIGN PATENT DOCUMENTS

| | | | |
|---|---|---|---|
| 004211346 | 10/1993 | Germany | 623/22 |
| 405344991 | 12/1993 | Japan | 623/18 |

*Primary Examiner*—Paul J. Hirsch
*Assistant Examiner*—Michael B. Priddy
*Attorney, Agent, or Firm*—Nutter, McClennen & Fish, LLP

[57] ABSTRACT

An acetabular prosthesis has a shell component that is implantable within bone and a liner component that is matable to the shell. The shell has a generally convex bone engaging outer surface and a generally concave inner surface. A groove is formed in the inner surface of the shell and extends about at least a portion of the inner circumference of the shell. The liner has an inner concave surface and an outer, convex surface with a shape complementary to and matable within the inner surface of the shell. One or more positive surface features is formed on the outer surface of the liner, adapted for selective mating with the groove of the shell. The liner may be joined to the shell by press fitting the two components together such that the positive surface features engage the groove.

18 Claims, 3 Drawing Sheets

ACETABULAR PROSTHESIS ASSEMBLY

CROSS-REFERENCE TO RELATED APPLICATIONS

Not applicable.

STATEMENT REGARDING FEDERALLY SPONSORED RESEARCH

Not applicable.

FIELD OF THE INVENTION

The invention relates to joint prostheses and more particularly to acetabular prostheses useful for partial or total replacement of the hip joint.

BACKGROUND OF THE INVENTION

Acetabular prostheses are known for use as a component for a total hip prosthesis.

Acetabular prostheses typically include two separate components, one of which is a cup or shell that is affixed within a cavity reamed in healthy bone of the acetabulum. The acetabular cup may have an external (i.e., bone-contacting) geometry that is appropriate for a given patient. The inner geometry of the acetabular cup is usually characterized by a smooth, generally spherical cavity. The acetabular cup is typically made of a metal or metal alloy. In some cases, however, polymeric acetabular cups are utilized.

A liner component is often mated with the inner geometry of the acetabular cup to provide a low friction bearing surface that articulates with a femoral head. The liner may have an outer, spherical surface that is of a size and shape to enable it to mate with the inner surface of the acetabular cup. The inner surface of the liner likewise is hemispherically shaped, having a smooth, low friction surface. As noted above, the femoral head seats within and articulates with the internal surface of the liner.

Acetabular cups are often made from a metal or metal alloy. Some designs, however, utilize polymeric cups. One polymer commonly used to form the liner is ultrahigh molecular weight polyethylene. However, it is also possible to fabricate the liner from other materials, including metals, metal alloys and ceramics.

Regardless of the materials and geometries used for the acetabular prosthesis, the acetabular cup and liner must be joined together, usually during the course of a surgical procedure. That is, a surgeon first implants the acetabular cup within the patient's acetabulum. Thereafter, the liner is separately affixed within the acetabular cup. A variety of liner designs exist and many are not symmetrical. Thus, the surgeon must determine the appropriate orientation of the liner with respect to the cup. Once the liner is properly oriented, it must remain so after affixation to the cup.

Some acetabular prosthesis designs do not permit easy mating of the liner to the cup; the mating of some designs can, in fact, be quite challenging. Specialized tools or separate components may be necessary to join these components or to permanently affix them together. These additional steps may render the attachment process more time-consuming and may introduce the possibility that the liner and the shell will become misaligned due to surgical technique or for other reasons. Further, there is always a possibility that the joinder mechanism may fail to achieve its objective to secure the two components to one another.

A number of patents describe acetabular prostheses designs that utilize a separate component to lock the liner and the shell together. Examples of such patents include U.S. Pat. Nos. 4,619,658; 4,770,658; 4,784,663; 4,969,910; 5,049,158; 5,171,285; 5,263,988; 5,425,779; 5,507,826; and 5,658,348.

Other known designs do not require a separate locking mechanism to join the liner and the cup. Instead, an interference fit or another form of mechanical engagement of the two components is relied upon. Examples of patents disclosing such attachment mechanisms include U.S. Pat. Nos. 4,172,296; 4,650,491; 5,376,122; 5,443,519; and 5,549,698.

Despite the acetabular prostheses designs that are known to exist, there is still a need for an acetabular prosthesis design that provides excellent attachment strength between the liner and the cup while at the same time providing ease of assembly without the need for additional assembly tools or components.

SUMMARY OF THE INVENTION

An acetabular prosthesis has a shell component that is implantable within bone and a liner component that is matable to the shell. The shell has a generally convex bone engaging outer surface and a generally concave inner surface. A groove is formed in the inner surface of the shell and extends about at least a portion of the inner circumference of the shell. The liner, which has a polar region and an equator region, has an inner concave surface and an outer, convex surface with a shape complementary to and matable within the inner surface of the shell. One or more positive surface feature is formed on the outer surface of the liner, adapted for selective mating with the groove of the shell. The liner may be joined to the shell by press fitting the two components together such that the positive surface features engage the groove.

The prosthesis may also have a structure to prevent rotation of the liner with respect to the shell after joinder of the two components. The anti-rotation mechanism may be in the form of one or more tabs in the outer surface of the liner, adjacent to the positive surface features. At least one recess is formed in the shell with a size and shape complementary to the tabs such that each tab is matable within one of the recesses.

One advantage of the prosthesis of the present invention lies in its ease of assembly and its ability to provide good attachment strength between the liner and the shell.

DETAILED DESCRIPTION OF THE INVENTION

The present invention provides an acetabular prosthesis with an effective and convenient mechanism for joining and securing the acetabular shell and liner components to each other. Referring to FIGS. 1 through 4, the acetabular prosthesis 10 includes an acetabular shell 12 and a liner 14 which are selectively attachable to one another through an interlocking engagement.

Figure 1:
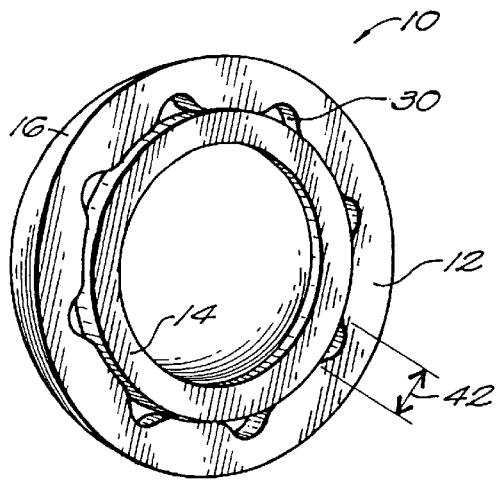
FIG. 1 is a bottom, perspective view of an acetabular prosthesis according to the present invention.
Figure 2:
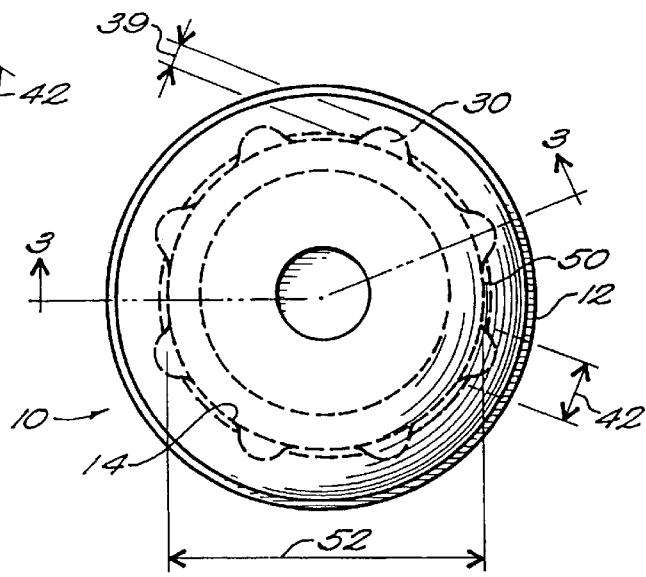
FIG. 2 is a bottom view of the acetabular prosthesis shown in FIG. 1.
Figure 3:
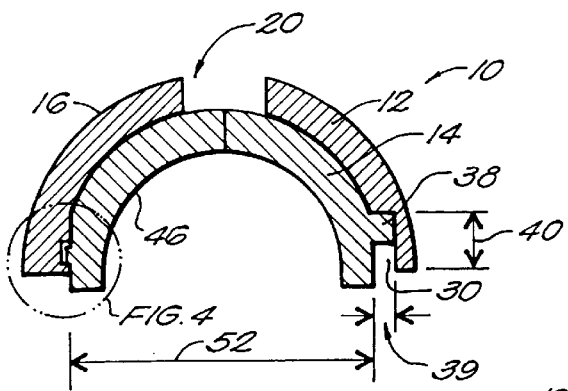
FIG. 3 is an elevated sectional view of the prosthesis shown in FIG. 2, at lines 3—3.
Figure 4:
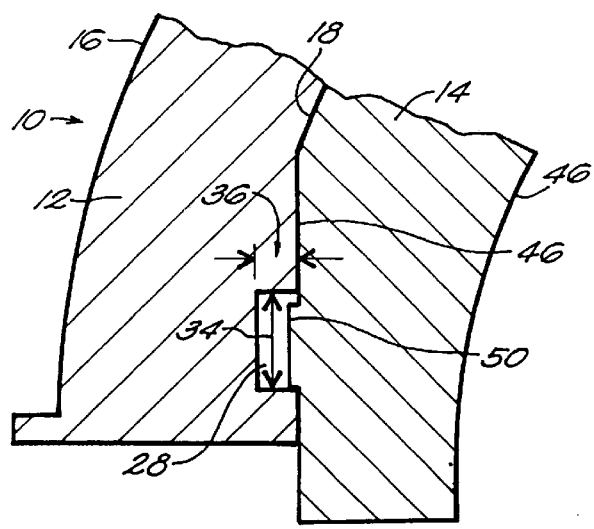
FIG. 4 is a detailed view of portion A of the prosthesis shown in FIG. 3.
Figure 5:
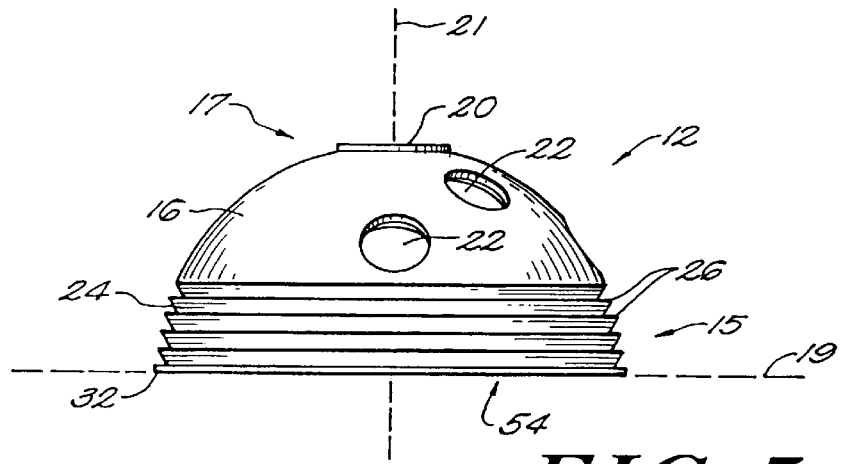
FIG. 5 is an elevated view of a shell component useful with the acetabular prosthesis of the invention.
Figure 6:
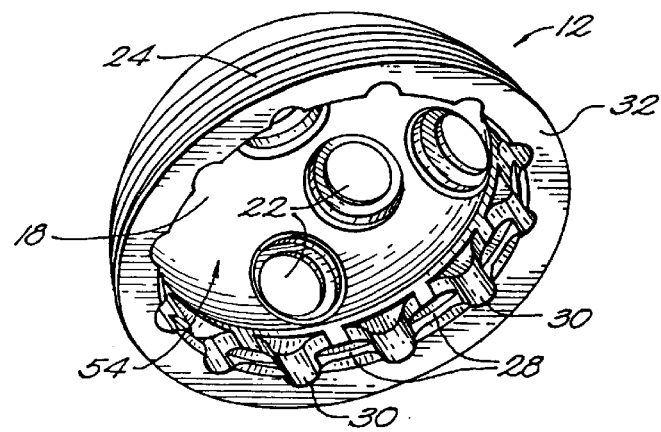
FIG. 6 is a perspective view of the shell component of FIG. 5.
Figure 7:
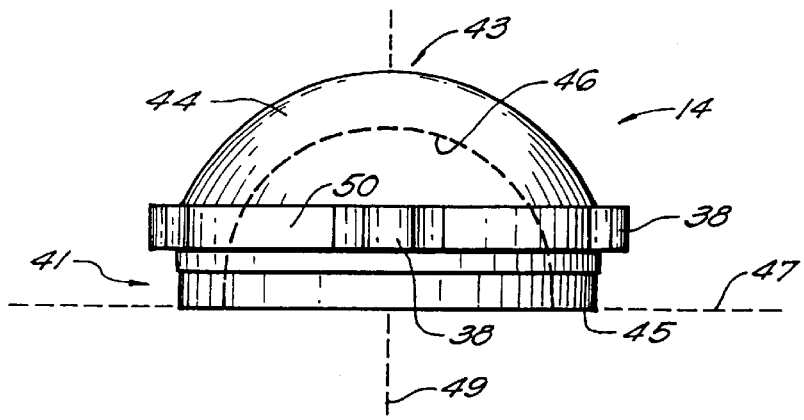
FIG. 7 is an elevated view of a liner component useful with the acetabular prosthesis of the invention.
Figure 8:
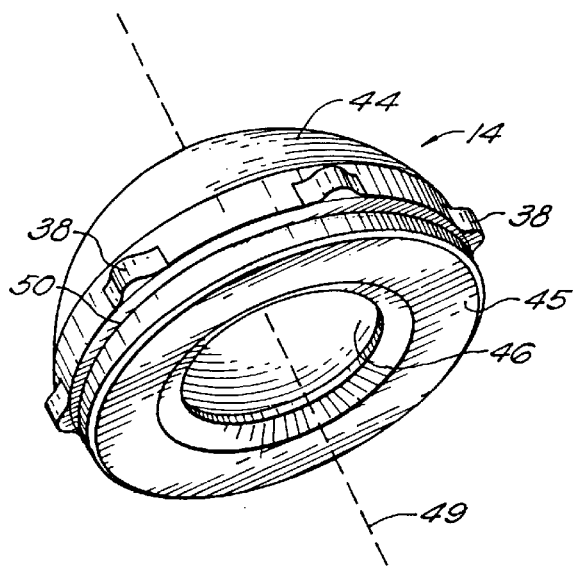
FIG. 8 is a perspective view of another liner component useful with the acetabular prosthesis of the present invention.
Figure 9:
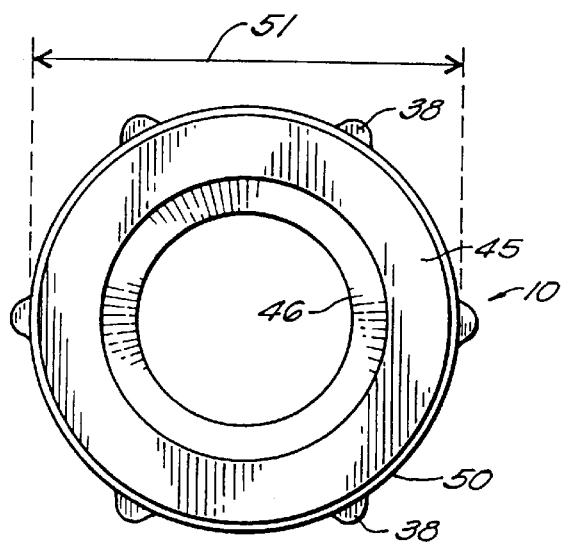
FIG. 9 is a bottom view of the liner component shown in FIG. 8.

The acetabular shell 12, illustrated in FIGS. 5 and 6, is a substantially hemispherical member having a generally convex outer bone-engaging surface 16. Opposite the outer surface 16 is a generally hemispherical, substantially concave liner surface 18. The shell may be characterized as having an equator region 15 and a polar region 17. Further, the shell includes an equatorial axis 19 and a polar axis 21.

The outer surface 16, as shown in FIGS. 5 and 6, may include an apical hole 20 for seating a bone screw, and one or more additional holes 22 extending therethrough. The outer surface of the shell may further include surface features 24, such as ridges 26, to optimize fixation to bone and/or to encourage bone ingrowth. Although ridges 26 are the only surface features illustrated, one of ordinary skill in the art will readily appreciate that a variety of additional surface features can be formed on the outer surface to optimize performance of the prosthesis.

The inner surface 18, as shown in FIGS. 1 through 4 and 6, includes a groove 28 that extends substantially parallel to the equatorial axis 19. The groove 28 may be continuous or it may be formed of discrete elements. Further, the groove 28 may extend partially or entirely around the circumference of the shell, either continuously or in discrete sections. In the embodiment illustrated in FIGS. 3 and 6, the groove 28 is disposed in the equatorial region 15, and is spaced from the rim 32 of the shell, in the direction towards the polar region 17. Further, the embodiment of FIG. 6 illustrates that the groove 28 is interrupted by recesses 30, which extend perpendicular to the equatorial axis 19.

In one embodiment, the groove 28 begins a distance of about 0.5 to 10 mm from the rim 32, in the direction towards the polar region 17. The dimensions of the groove will vary depending upon variables such as the dimensions of the shell, the dimensions of the liner and the dimensions of certain surface features present on the liner. In one embodiment, however, the groove 28 has a height 34 in the range of about 1 to 3 mm and a depth 36 of about 0.2 to 1.5 mm.

The grooves may be separated from each other by about 0° to 180°, with 0° separation representing a continuous groove.

The recesses 30 are intended to seat anti-rotation tabs 38 present on the liner 14, as discussed below, to prevent rotation of the liner 14 relative to the acetabular shell 12. The recesses 30 extend from the rim 32 towards the pole region 17. The height 40 of the recesses may be about 2 to 8 mm while their width 42 is about 1 to 3 mm. The depth 39 of the recesses may be in the range of about 0.5 to 4 mm.

The shell 12 can be made from a variety of suitable materials. Generally, however, it is made from metals or metal alloys known to those having ordinary skill in the art.

The liner 14 has an equatorial region 41 and a rim 45. Opposite the equator region 41 is a polar region 43. An equatorial axis 47 of the liner extends parallel to the equatorial region 41 while a polar axis 49 extends perpendicular to the equatorial axis 47. The liner also has a convex outer surface 44, which is substantially hemispherically shaped and complementary to inner surface 18 of shell 12. The liner 14 also has a concave inner surface 46 which is intended to seat a femoral head of a hip prosthesis (not shown). One of ordinary skill in the art will appreciate that the inner surface 46 should be a smooth, low friction surface.

The liner 14, as illustrated in FIGS. 3, 4 and 7–9, includes one or more anti-rotation tabs 38 which protrude from the outer surface 14. The tabs 38 can be of virtually any shape that is complementary to and matable within the recesses 30 of the shell 12. Accordingly, the tabs 38 protrude from the outer surface of the liner by about 0.5 to 4 mm and have a width in the range of about 1 to 3 mm.

Tabs 38 may be positioned at virtually any location on the outer surface 44 of the liner 14. In one embodiment, the tabs 38 are positioned adjacent to the equatorial region 41, spaced approximately 0.5 to 1.0 from the rim 45 in the direction towards the polar region 43.

As noted above, the anti-rotation tabs 38 cooperate with the recesses 30 to prevent rotation of the liner 14 relative to the shell 12. No specific number of anti-rotation tabs 38 and recesses 30 is necessary to prevent rotation of the liner 14 relative to the shell 12 since any number will accomplish this objective. Generally, however, more than one anti-rotation tab 38 is present and from four to nine anti-rotation tabs can be used, depending upon the size of the liner and the shell.

The outer surface 44 of the liner 14 also includes a raised ridge 50. The ridge cooperates with the groove 28 to selectively attach the liner to the shell. The ridge protrudes from the outer surface 44 of the liner 14 by a distance sufficient to prevent noninterfering insertion of the liner 14 within the shell 12. That is, the outer diameter 51 of the liner, measured at the ridge 50, is greater than the inner diameter 52 of the opening 54 of the shell. The ridge 50 should protrude from the outer surface 18 of the liner by a distance in the range of about 0.1 to 1.0 mm, and preferably about 0.1 to 0.6 mm. Similarly, the outer diameter 51 of the liner measured at the ridge 50 should exceed the inner diameter 52 of the opening 54 by about 0.1 to 1.5 mm.

The ridge 50 may be a continuous structure, or it may be present on the outer surface of the liner in discrete sections. Further, the ridge 50 may extend partially or completely about the circumference of the liner, either continuously or in discrete sections.

Figure 10A:
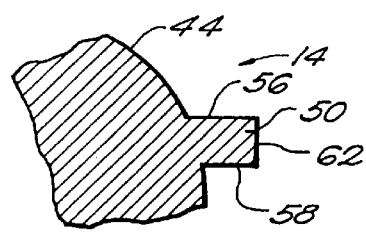
FIG. 10A is a detailed sectional view of a portion of a liner constructed according to one embodiment of the present invention.
Figure 10B:
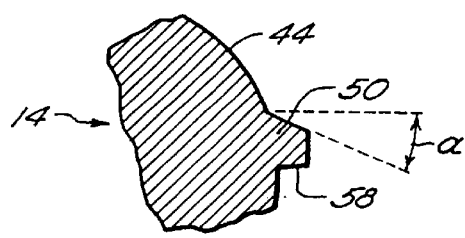
FIG. 10B is a detailed sectional view of a portion of a liner constructed according to another embodiment of the present invention.
Figure 10C:
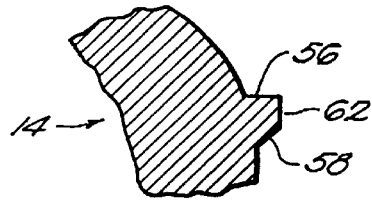
FIG. 10C is a detailed sectional view of a portion of a liner constructed according to another embodiment of the invention.

The ridge 50 may take on a variety of shapes. As shown in FIGS. 10A–10C, the ridge is comprised of a superior wall 56, an inferior wall 58 and an end wall 62. The end wall 62 is generally parallel to the polar axis 49 of the liner as shown in FIG. 10A, or it may conform in shape to the curvature of the outer surface 44 of the liner. Moreover, the end wall 62 may be spaced apart from the outer surface 44 of the liner by about 0.1 to 0.6 mm. The superior wall 56 may be parallel to the equatorial axis 47 of the liner (FIG. 10A), or it can be angled with respect to the equatorial axis 47 of the liner (FIG. 10B). In one embodiment, the superior wall 56 forms a downwardly sloping, acute angle ($\alpha$) with a line drawn parallel to the equatorial axis 47. The range of angle (a) may be about 0 to 45 degrees. Similarly, the inferior wall 60 may extend parallel to the equatorial axis 47 (FIG. 10A), or it may be angled with respect to the equatorial axis (FIG. 10C). One of ordinary skill in the art will readily appreciate that the ridge 50 may be present in numerous alternative geometries without departing from the scope of the invention.

As noted above, the invention provides a reliable and convenient attachment mechanism for selectively joining an acetabular shell to a liner component. To attach these two components together, the anti-rotation tabs 38 of the liner 14 are aligned with the recesses 30 of the shell 12. This orientation allows the outer surface of the liner to be inserted through opening 54 into the inner surface of the shell 12. During the insertion process a superior edge 56 of the ridge 50 will encounter the inferior wall 58 of rim 32, preventing further insertion of the liner within the shell. This resistance to further insertion can be overcome by applying additional force to the liner, enabling the force fitting of the ridge 50 within the opening 54. The force fitting can be accomplished by expansion of the opening, slight deformation of the ridge, or by contraction of the liner. Once the initial resistance to further insertion is overcome, further force will cause the ridge 50 to be seated within groove 28 enabling the liner to be mechanically engaged within the shell.

It is understood that various modifications may be made to the invention described herein without departing from the intended scope thereof. Further, all dimensions are intended to serve only as examples; one of ordinary skill in the art may easily determine additional or alternative dimensions. All references cited herein are expressly incorporated by reference in their entirety.

What is claimed:

1. An acetabular cup prosthesis, comprising:
    a shell component having a generally convex bone-engaging outer surface and a generally concave inner surface with a groove formed in the inner surface thereof and extending about at least a portion of the circumference of the inner surface of the shell component;
    a liner component having an inner, concave surface and an outer, convex surface with a shape complementary to and matable within the inner surface of the shell component, the liner component having a polar region and an equator region;
    at least one positive surface feature formed on the outer surface of the liner component, the at least one positive surface feature being selectively matable with the groove of the shell and having (i) an end wall spaced apart from the outer, convex surface and (ii) opposed side walls connecting the end wall to the outer, convex surface of the shell component wherein the opposed side walls comprise a superior side wall and an inferior side wall, the superior side wall forming a downwardly sloping acute angle with an equatorial line drawn parallel to an equatorial axis of the liner;
    at least one anti-rotation tab member formed on the outer surface of the liner component, adjacent to the at least one positive surface feature; and
    at least one recess formed in the inner surface of the shell component the at least one recess having a size and shape complementary to the at least one anti-rotation tab member such that each of the at least one recesses is effective to matingly engage one of the at least one anti-rotation tab members.

2. The prosthesis of claim 1, wherein the groove extends about the entire circumference of the inner surface of the shell component.

3. The prosthesis of claim 1, wherein the at least one positive surface feature is adjacent the equator region of the liner component.

4. The prosthesis of claim 1, wherein the at least one positive surface feature comprises a plurality of discrete positive surface features that are formed on the outer convex surface of the liner component.

5. The prosthesis of claim 2, wherein the at least one positive surface feature comprises a single positive surface feature extending continuously about the entire circumference of the liner component.

6. The prosthesis of claim 1, wherein the end wall extends substantially parallel to the outer, convex surface of the shell component.

7. The prosthesis of claim 1, wherein the angle is in the range of 0 to 45 degrees.

8. The prosthesis of claim 1, wherein at least a portion of each of the at least one anti-rotation tab members and the at least one recess is substantially hemispherically shaped.

9. The prosthesis of claim 1, wherein the groove has a height in the range of about 1 to 3 mm.

10. The prosthesis of claim 9, wherein the groove has a depth in the range of about 0.2 to 1.5 mm.

11. The prosthesis of claim 9, wherein the end wall of the at least one positive surface feature is spaced apart from the outer surface of the liner by a distance in the range of about 0.1 to 0.6 mm.

12. The prosthesis of claim 11, wherein each of the at least one positive surface features has a height in the range of about 1 to 3 mm.

13. The prosthesis of claim 1, wherein the liner component and shell component are matable to one another by forcing the liner component within the shell component to enable the at least one positive surface feature to be engaged within the groove.

14. The prosthesis of claim 1, wherein a diameter of the liner component measured from the end wall of the at least one positive surface feature is greater than an inner diameter of the shell component measured at an equator of the shell component.

15. An acetabular cup prosthesis, comprising:
    a shell component having a generally convex bone-engaging outer surface and a generally concave inner surface with a groove formed in the inner surface thereof and extending about of the circumference of the inner surface of the shell component;
    a liner component having an inner concave surface and an outer, convex surface with a shape complementary to and matable within the inner surface of the shell component, the liner component having a polar region and an equator region;
    a continuous positive surface feature formed on and extending about the circumference of the outer surface of the liner component, the continuous positive surface feature being selectively matable with the groove of the shell;
    at least one anti-rotation tab member formed on the outer surface of the liner component, adjacent to the continuous positive surface feature; and
    at least one recess formed in the inner surface of the shell component, the at least one recess having a size and shape complementary to the at least one anti-rotation tab member such that each of the at least one recesses is effective to matingly engage one of the at least one anti-rotation tab members.

16. The prosthesis of claim 15, wherein the groove has a depth in the range of about 0.2 to 1.5 mm.

17. The prosthesis of claim 16, wherein the groove has a height in the range of about 1 to 3 mm.

18. The prosthesis of claim 16, wherein an end wall of the continuous positive surface feature is spaced apart from the outer surface of the liner by a distance in the range of about 0.1 to 0.6 mm.

* * * * *